United States Patent [19]

Holvoet et al.

[11] Patent Number: 4,595,441
[45] Date of Patent: Jun. 17, 1986

[54] FABRICATION METHOD FOR DISPOSABLE ARTICLES AND A LIQUID-ABSORBING DISPOSABLE ARTICLE

[75] Inventors: Marcel Holvoet, Louviers; Sem Mitrani, Ris Orangis; Raymond Pigneul, Durrenentzen, all of France

[73] Assignee: Beghin-Say S.A., Thumeries, France

[21] Appl. No.: 552,147

[22] PCT Filed: Feb. 3, 1983

[86] PCT No.: PCT/FR83/00023

§ 371 Date: Nov. 1, 1983

§ 102(e) Date: Nov. 1, 1983

[87] PCT Pub. No.: WO83/03051

PCT Pub. Date: Sep. 15, 1983

[30] Foreign Application Priority Data

Mar. 2, 1982 [FR] France ............... 82 03409

[51] Int. Cl.⁴ .................. B32B 31/08; B65C 9/25
[52] U.S. Cl. .................. 156/265; 156/164; 156/256; 156/301; 156/324; 156/525; 156/554; 156/559
[58] Field of Search .............. 156/163–164, 156/251, 254, 256, 258, 260, 264–265, 269, 290, 301–303, 324, 552, 554, 559, 525

[56] References Cited

U.S. PATENT DOCUMENTS 3,758,363 9/1973 Frick .................. 156/301

FOREIGN PATENT DOCUMENTS 2246680 5/1975 France .

Primary Examiner—Edward Kimlin
Assistant Examiner—Merrell C. Cashion, Jr.
Attorney, Agent, or Firm—A. W. Breiner

[57] ABSTRACT

A fabrication method for a disposable article and a disposable article for absorbing liquids.

This method consists in cutting an impermeable foil (35) so as to form two strips (35a) and (35b) in the median zone of said foil along a tracing of a sequence of equal straight-line segments parallel to the longitudinal axis of the foil and staggered alternatingly on either side of said axis. The strip (35a) is laterally shifted by a distance slightly less than the distance between the segments located on either side of the axis XX'. The strip (35b) follows a path which is longer than that of the strip (35a) by the repeat of the cut-out. The strips (35a) and (35b) then are deposited on the absorbing portions (34) in such a manner that the permeable zone is located in the central region of said portion.

The obtained sheath is cut into individual articles.

6 Claims, 15 Drawing Figures

FABRICATION METHOD FOR DISPOSABLE ARTICLES AND A LIQUID-ABSORBING DISPOSABLE ARTICLE

The object of the present invention is a continuous fabrication method for a disposable article to absorb liquids, using a machine comprising a device for paper-pulp grinding, a section shaping a continuous strip of ground pulp, a device for cutting said strip into a series of absorbing materials.

The present invention also relates to disposable articles to absorb liquids, in particular body liquids such as blood or urine.

These articles can be dressings, menstrual napkins, diapers, or complete changes for babies or incontinent adults.

In general such articles are stratified and consist of a pad of cellulose fibers making it possible to absorb and retain liquids, and placed between a liquid-permeable foil and a plastic foil acting as a barrier against said liquids.

Most often the permeable foil is a non-woven material consisting of artificial and/or synthetic fibers. Reserach in recent years has been widely applied to the structure of these non-woven materials; depending on the fabrication procedure and the kind of fibers used, non-woven materials rapidy transmitting a liquid but retaining little humidity after the ligquid has been absorbed by a pad of cellulose fibers can be made.

Accordingly, the surface of the absorbing articles in contact with the user's skin stays slightly moist; comfort is increased and the danger of irritation is substantially decreased.

The plastic foil blocking the liquids as a rule is an embossed polyethylene foil bonded to the non-woven material along the article's longitudinal edge; it protects clothes and underwear.

In some cases, as for complete changes, the polyethylene foil is folded back along the periphery of the article to form a narrow hydrophobic and impermeable strip on the side of the non-woven material; therefore, when the article is well applied on the user, the liquids to be absorbed remain within the zone defined by the polyethylene strip. Danger of leakage is reduced, but the major drawback is that the user's skin is humid over the entire surface of the article.

Other articles such as menstrual napkins are totally enveloped by a non-woven material and are provided between this non-woven material and the absorbing pad with a U-shaped plastic foil protecting both the inside of the articles and its sides. Recently, menstrual napkins have become commercially available which comprise a plastic foil of which the legs of the U are folded back along the longitudinal edges so as to form a kind of gutter; thereby the lateral leaks are practically eliminated, but on the other hand the article ends comprise no barrier at all against the liquids.

To palliate the drawbacks of the present articles, the present invention proposes a new structure whereby an impermeable foil provided with a liquid-permeable zone is placed between the non-woven material making contact with the user's skin and the absorbing material, said zone being located centrally with respect to the upper side of the absorbing material.

In the invention, the fabrication method is characterized in that:

(a) an impermeable foil is unwound from a supply spool and while forming two continuous strips passes into a device cutting it in its median zone along a lay-out consisting of a series of straight-line sections parallel to the longitudinal axis of the foil, said straight-line sections being:
  alternatingly staggered on either side of said axis,
  shifted with respect to each other, with the distance between two consecutive sections located on the same side of the foil axis exceeding the length of the sections,
and of which the ends are connected by sections intersecting the foil axis at their center,
(b) the first strip is laterally offset by a distance slightly less than the distance between the sections located on either side of the foil axis,
(c) the second strip follows a longer path than the first, exceeding the length of the first by the repeat of the cut-out,
(d) the two strips then are deposited on absorbing materials in such a manner that the open zones bounded by said strips are located in the central region of the absorbing material,
(e) the sheath so obtained is cut into individual articles.

In a variation of the invention the two strips are heat-sealed or bonded along the article's longitudinal edges to a continuous impermeable foil which provides the inside.

In a variation of the invention, the impermeable foil is micro-punctured before being cut, for instance using a needle-studded roller with a foam-support roller on the other side, both rollers being the same width as the foil. This embodiment retains liquids especially satisfactorily while avoiding any danger of steeping.

In another variation of the invention, whether or not combined with those above, the cut-out is provided by a knife means tracing a sinusoid on the moving impermeable foil, the amplitude of the sinusoid corresponding to the half-width of the permeable zone and the half wavelength being the length of the permeable zone.

Another object of the invention is a disposable article for absorbing liquids and comprising an absorbing material of which at least the upper surface consists of a liquid-permeable non-woven substance, characterized in that a liquid-impermeable foil is placed between the absorbing material and the non-woven substance, this foil consisting at least of two cut-out strips which are assembled to form a permeable zone of oblong shape and baring at least 50% of the absorbing material at its central region. Another plastic foil forms the liquid-barrier at the internal surface of the article. The ends of the article are heat-sealed or bonded in such a manner they prevent any liquid from moving from the absorbing material toward the upper or lower surfaces. Preferably the permeable zone is less than 80% of the total surface of the absorbing material.

Thanks to the present invention, disposable articles for absorbing liquids are henceforth available wherein the liquid is contained in an impermeable pocket; the liquids cannot move up the sides or near the ends.

In general these articles are manufactured with machines equipped with a paper-pulp grinding apparatus, a section shaping a continuous strip of ground pulp, an apparatus cutting said strip into a succession of separate absorbing materials.

In one embodiment of the invention, the impermeable foil strips are combined by heat-sealing or bonding with a non-woven material before they are applied to the absorbing materials.

Other advantages and features of the invention are stated in the description below of several illustrative embodiments:

Figure 1:
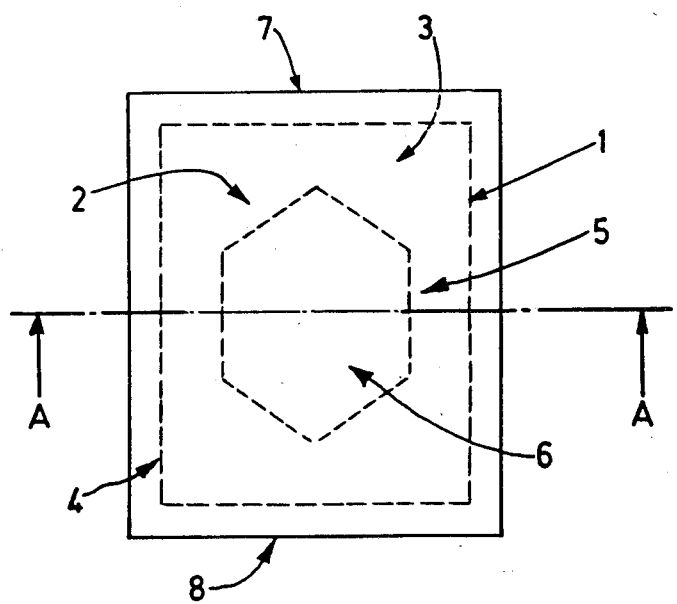
FIG. 1 is a top view of an article in a first embodiment of the invention.
Figure 2:
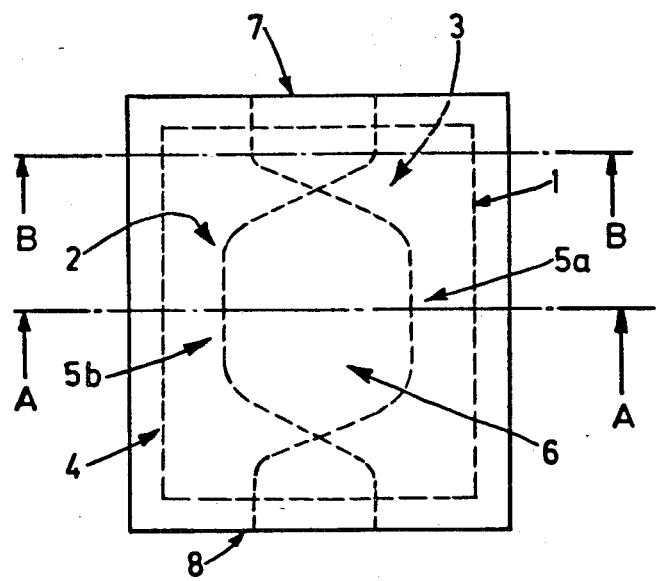
FIG. 2 is a top view of an article of which the central absorption zone is bounded by two strips cut from an impermeable foil.
Figure 3:
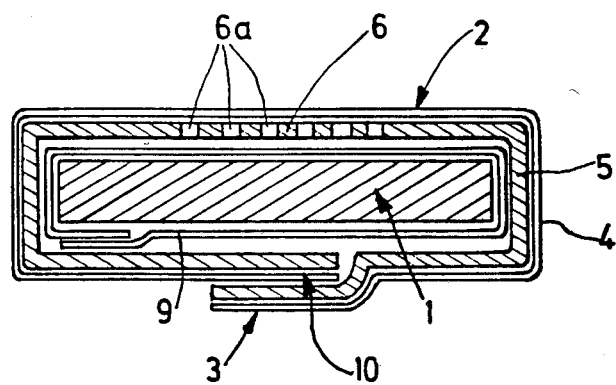
Figure 4:
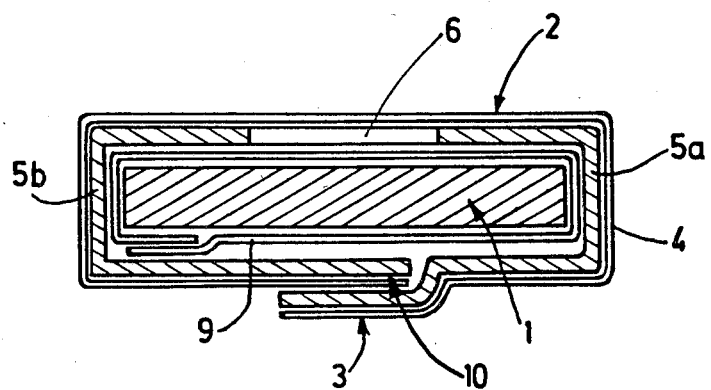
Figure 5:
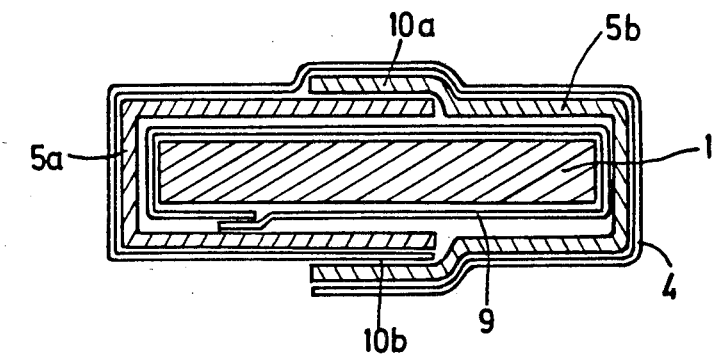
Figure 6:
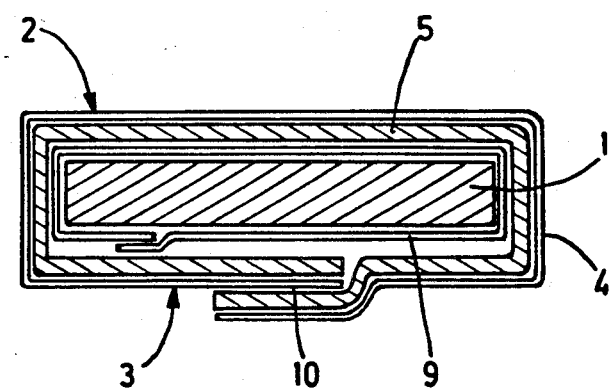
Figure 7:
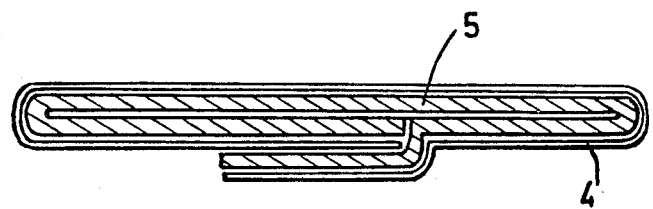
Figure 8:
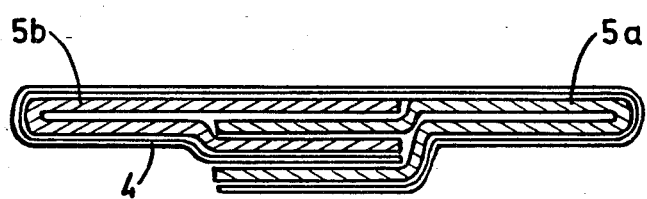
Figure 9:
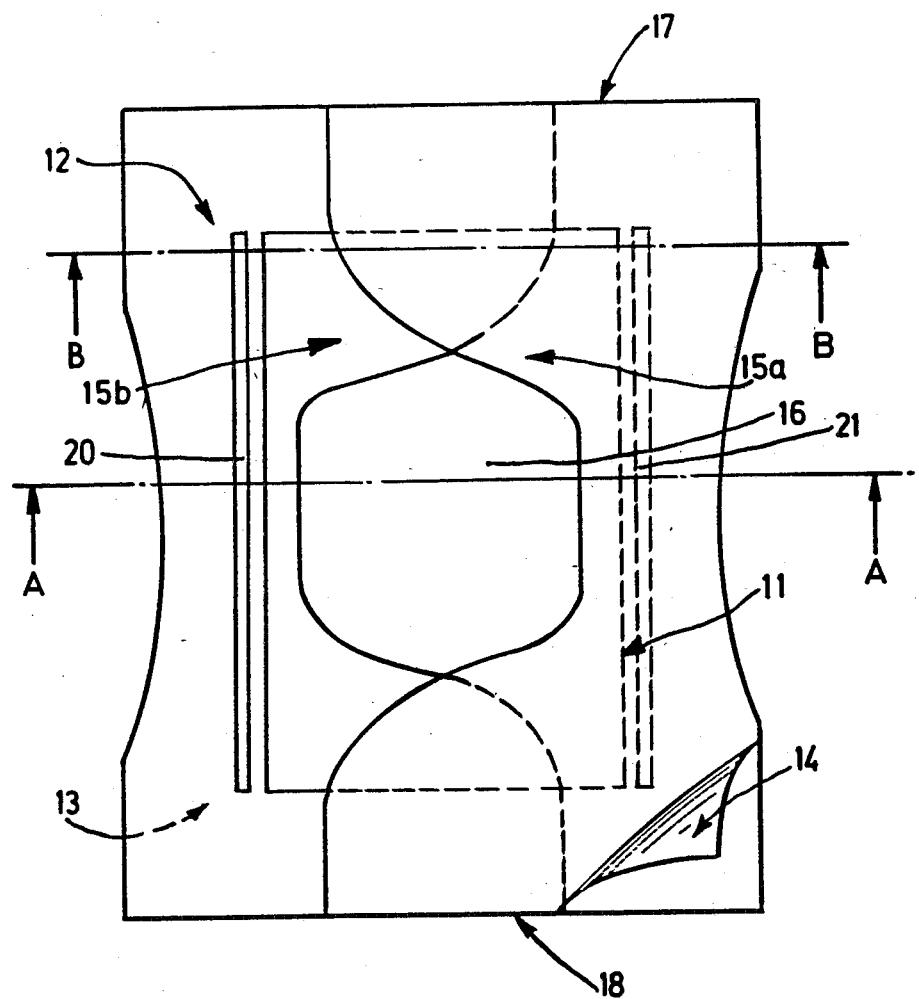
Figure 10:
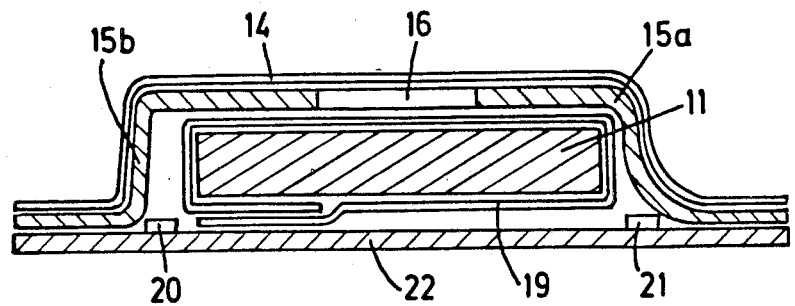
Figure 11:
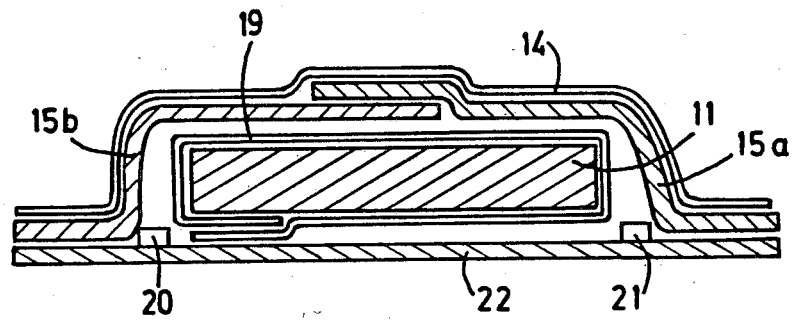
Figure 12:
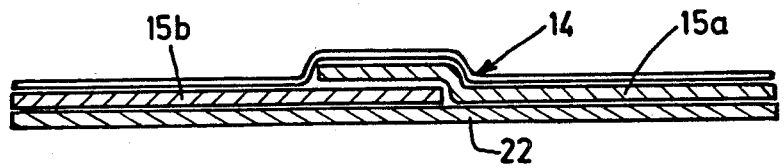
Figure 13:
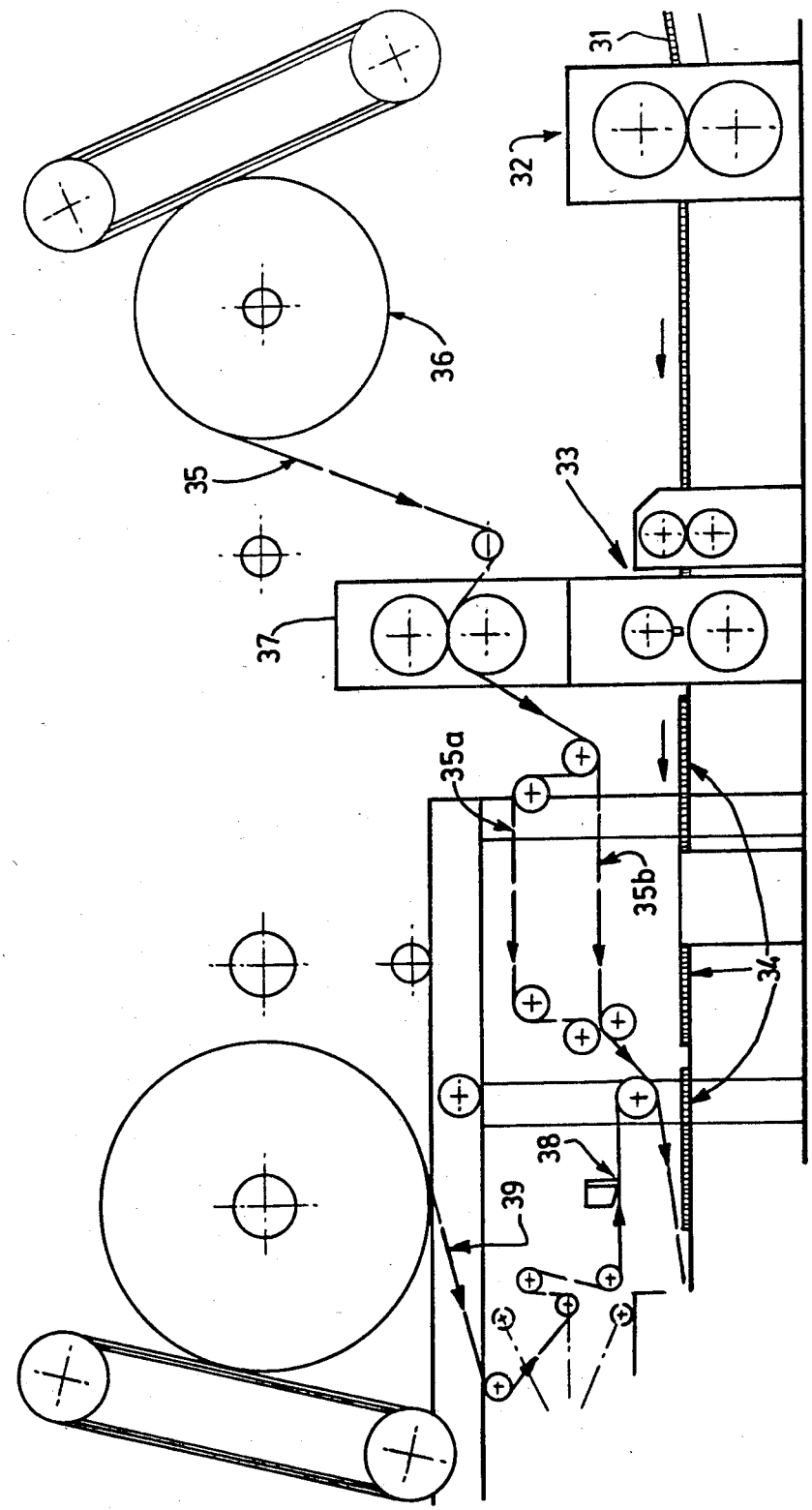
Figure 14:
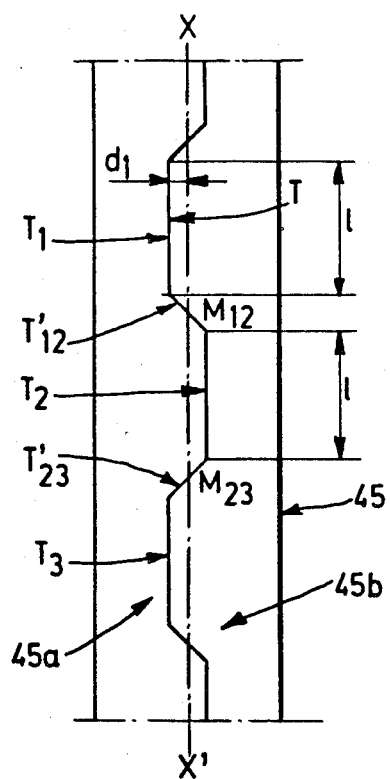
Figure 15:
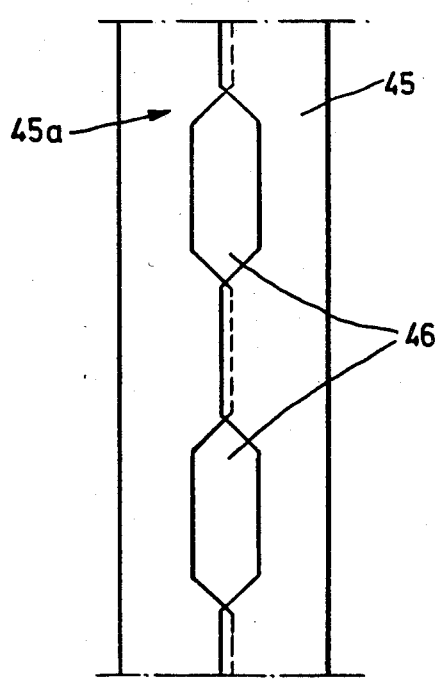

FIG. 3 is a cross-section of FIG. 1 along AA.
FIG. 4 is a cross-section of FIG. 2 along AA.
FIG. 5 is a cross-section of FIG. 2 along BB.
FIG. 6 is a cross-section of FIG. 1 along BB.
FIG. 7 is an end view of FIG. 1.
FIG. 8 is an end view of FIG. 2.
FIG. 9 is a top view of a complete change according to the invention.
FIG. 10 is a cross-section of FIG. 9 along AA.
FIG. 11 is a cross-section of FIG. 9 along BB. FIG. 12 is an end view of FIG. 9.
FIG. 13 is a functional schematic of a machine to make an article of the invention,
FIG. 14 is a top view of a foil cut-out along a tracing allowing to form absorption zones.
FIG. 15 is a top view of two strips cut from a foil per FIG. 14 and so combined they form open zones.

FIGS. 1 and 2 show an article of the invention comprising an absorbing portion (1) with an upper surface (2) and a lower surface (3), and consisting of a liquid-permeable non-woven material (4). A liquid-impermeable foil (5) is placed between the absorbing portion (1) and the non-woven material (4) on the upper surface (2). This foil (5) is provided with a liquid-permeable zone (6) and can consist of two half-foils (5a) and (5b). The article, furthermore, has two ends (7) and (8).

FIG. 3 is a cross-section of FIG. 1 along AA; the foil (5) comprises a zone (6) with a multiplicity of perforations (6a). The foil (5) is clad with a non-woven material (4), and its longitudinal edges are bonded or heat-sealed at (10).

FIG. 4 is a cross-section of FIG. 2 along AA; the impermeable foil (5) consists of two half-foils (5a) and (5b) which are so cut out and combined that they form an oblong opening (6).

The half foils (5a) and (5b) clad with a non-woven material (4) completely surround the absorbing portion (1) and are bonded or heat-sealed (at 10) on the lower surface (3) so that this absorbing portion (1) is completely enveloped except in zone (6).

Advantageously the absorbing portion (1) is wrapped in a cotton-wool foil (9) assuring good liquid diffusion. The cotton-wool foil (9) is placed between the absorbing portion (1) and the impermeable foil (5a, 5b).

FIG. 5 is a cross-section of FIG. 2 along BB; the two half foils (5a) and (5b) are bonded or heat-sealed near the upper surface (2) and the lower surface (3) so as to completely enclose the absorbing portion (1) near the ends (7) and (8), at (10a) and (10b).

FIG. 6 is a cross-section of FIG. 1 along BB; the foil (5) completely encloses the absorbing portion (1) and its longitudinal edges are bonded or heat-sealed near the lower surface (3) of the article.

FIGS. 7 and 8 are end views of the articles shown in FIGS. 1 and 2; the sheet (5)—or the two half sheets (5a) and (5b)—are transversely bonded or heat-sealed to themselves so as to close the ends (7) and (8) of the article of the invention.

Thus, the liquids are absorbed in the absorbing portion (1) through the zone (6), and diffuse throughout the entire absorbing portion (1), in particular into the parts enclosed by the impermeable foil (5); the ends (7) and (8) being closed, the liquids cannot rewet the upper surface (2) of the article and the non-woven material (4) if at all stays humid only in the zone (6).

FIGS. 9 through 12 are a top view and cross-sectional views of a complete change of which the absorbing portion (11) enclosed in a sheet of cotton-wool (19) is fixed on an impermeable foil (22). Thin strips are bonded in the stretched state on the flim (22) along the longitudinal edges of the absorbing portion (11). Two strips (15a) and (15b) cut from an impermeable foil are mounted on the absorbing portion (11) and bound a liquid-passing zone (16).

The strips (15a) and (15b) totally overlap near the ends of the absorbing portion (11). The ends (17) and (18) of the complete change are closed, the foils (15a), (15b) and (22) being transversely bonded or heat-sealed. Furthermore, the longitudinal edges of the complete change also are bonded or heat-sealed.

The upper surface (12) of the complete change consists of a liquid-permeable non-woven material (14) which is bonded or heat-sealed on its entire surface to the two strips (15a) and (15b).

FIG. 13 is a functional schematic of the fabrication method for an article of the invention. A ribbon of ground pulp (31) enclosed in a sheet of cotton-wool moves between embossing rollers (32) and then into a device cutting the ribbon into a series of separate absorbing portions (34).

An impermeable foil (35) is wound off a main spool (36) and passes into a cut-out device (37); two half-strips (35a) and (35b) are obtained. The strip (35a) moves over a longer path than the strip (35b) so as to form the zones (6) (FIG. 2). Immediately before being applied on the absorbing portions (34), the strips (35a) and (35b) are fastened by a bonding feed (38) to the non-woven material (39).

The separate absorbing portions (34) are moved in manner known per se on a plastic foil which will be the rear surface of the complete change.

In this manner a continuous sheath is obtained, which consists of a series of absorbing portions enclosed in an envelope impermeable everywhere excep in their central upper regions; illustratively the individual articles are separated by a heat-cutting device. Again it is possible to transversely heat-seal the articles and then to separate them using a rotating knife means.

FIGS. 14 and 15 show how to make two half-strips (45a) and (45b) from one foil (45). The foil (45) is cut along a tracing (T) consisting of a sequence of straight lines ($T_1$, $T_2$, $T_3$ . . . ,) of the same length 1 and parallel to the longitudinal axis XX' of the foil (45), arranged in staggered manner on either side of XX' and shifted with respect to each other, the distance between two segments ($T_1$) and ($T_3$) located on the same side of XX' exceeding 1. The ends of two segments ($T_1$) and ($T_2$) located on either side of XX' are connected by a segment $T'_{12}$ of which the center $M_{12}$ is located on the axis XX'.

The strip (45b) is laterally shifted by a distance slightly exceeding $d_1$ (the distance between the segments ($T_1$) ($T_2$) ($T_3$) and the XX' axis) and then is longitudinally shifted by a length to the cutting repeat (T) so that two segments such as ($T_1$) and ($T_2$) are symmetrical with respect to the XX' axis.

In this manner a series of open zones (46) is formed, the strips (45a) and (45b) overlapping solely between these zones (46).

Illustratively, a polyethylene foil 300 mm wide is used to make a zone (46) of which the biggest dimension is 315 mm and the width 110 mm, the article dimensions being 550×350 mm. Segments $(T_1)$, $(T_2)$, $(T_3)$ ..., 205 mm long and parallel to the XX' axis are cut out and are 30 mm from it.

The $(T_1)$, $(T_2)$, $(T_3)$ segments are arranged in such a manner that the distance $M_{12}$ $M_{23}$ between two segments $(T'_{12})$, $(T'_{23})$ is 275 mm. The cut-out repeat is 265 mm. By laterally shifting the strip (45b) by 50 mm and by longitudinally shifting it by one repeat, that is 265 mm, a series of open zones (46) 110 mm wide and of maximum length of 315 mm is obtained.

The two strips (45a) and (45b) overlap longitudinally over 10 mm near the XX' axis.

We claim:

1. A continuous method for the fabrication of disposable articles designed to absorb liquids comprising the steps of
   (a) cutting a continuous impermeable foil (45) into first and second continuous strips (45a,45b) and in its median zone along a lay-out to provide a cut-out area comprising a series of straight-line sections $(T_1, T_2, T_3 ...)$ parallel to the longitudinal axis (XX') of the foil, whereby said straight-line sections are alternatingly staggered on either side of said axis with the distance between two consecutive sections located on the same side of the foil axis exceeding the length (l) of the sections, with the ends of said sections being connected by connecting sections $(T_{12}', T_{23}'...)$ intersecting the foil axis at their center, said first strip (45b) being laterally shifted by a distance slightly less than the distance $(d_1)$ between the straight line section and the longitudinal axis, and then longitudinally by a length equal to the cutting repeat (T) so that two straight line sections are symmetrical with respect to said axis, with said second strip (45a) following a longer path than the first (45b) and exceeding the length of said first strip by the repeat (T) of the cut-out;
   (b) depositing said first and second strips on an absorbing material in such a manner whereby open zones bounded by said strips are located in the central region of said absorbing material; and
   (c) cutting the sheath so obtained into individual articles.

2. The method of claim 3 wherein said impermeable foil strips are combined with a non-woven material before being deposited on said absorbing material.

3. The method of claim 4 wherein said impermeable foil strips are fastened by means of a bonding feeder onto said non-woven material immediately before they are applied on the absorbing material.

4. The method of claim 3 wherein said impermeable foil strips are heat-sealed near the lower surface of the absorbing material in a direction parallel to the longitudinal axis of the foil.

5. The method of claim 3 wherein impermeable foil strips are heat-sealed or bonded along the longitudinal edges of the article to an impermeable plastic foil constituting the lower surface of the article.

6. The method of claim 3 wherein the ends of each article are transversely heat-sealed before the sheath is severed into individual articles.

* * * * *